(12) United States Patent
Girsh

(10) Patent No.: US 8,658,218 B2
(45) Date of Patent: Feb. 25, 2014

(54) COMPOSITION WITH ANTI-INFLAMMATORY, PROTEIN SYNTHESIZING, TREATMENT OF ENZYME DEFICIENCY, ACTIVATING GENETIC THERAPY AND ANTI-CANCER ACTIVITY AND METHODS OF USE

(75) Inventor: Leonard S. Girsh, Naples, FL (US)

(73) Assignee: Immunopath Profile, Inc., Naples, FL (US)

( * ) Notice: Subject to any disclaimer, the term of this patent is extended or adjusted under 35 U.S.C. 154(b) by 0 days.

(21) Appl. No.: 13/368,672

(22) Filed: Feb. 8, 2012

(65) Prior Publication Data

US 2012/0141594 A1 Jun. 7, 2012

Related U.S. Application Data

(63) Continuation of application No. 12/872,648, filed on Aug. 31, 2010, now Pat. No. 8,119,596, which is a continuation of application No. 10/765,664, filed on Jan. 26, 2004, now Pat. No. 7,790,678, which is a continuation-in-part of application No. 10/752,298, filed on Jan. 5, 2004, now abandoned, said application No. 12/872,648 is a continuation of application No. 10/765,664, filed on Jan. 26, 2004, now Pat. No. 7,790,678, which is a continuation-in-part of application No. 09/639,859, filed on Aug. 16, 2000, now Pat. No. 6,974,796.

(60) Provisional application No. 60/437,939, filed on Jan. 3, 2003, provisional application No. 60/442,278, filed on Jan. 24, 2003, provisional application No. 60/447,779, filed on Feb. 13, 2003, provisional application No. 60/448,003, filed on Feb. 18, 2003, provisional application No. 60/448,497, filed on Feb. 19, 2003, provisional application No. 60/149,338, filed on Aug. 17, 1999.

(51) Int. Cl.
- *A61K 35/34* (2006.01)
- *A61K 33/30* (2006.01)
- *A61K 38/39* (2006.01)
- *A61K 38/00* (2006.01)

(52) U.S. Cl.
USPC ........... 424/548; 424/643; 424/702; 424/766; 514/54; 514/13.3; 514/17.2

(58) Field of Classification Search
USPC ........... 424/548, 766, 702, 643; 514/17.2, 13, 514/54, 13.3
See application file for complete search history.

(56) References Cited

U.S. PATENT DOCUMENTS

| | | |
|---|---|---|
| 3,400,199 A | 9/1968 | Balassa |
| 4,145,447 A | 3/1979 | Fisher et al. |
| 4,562,080 A | 12/1985 | Tenn |
| 4,752,618 A | 6/1988 | Mascioli et al. |
| 4,857,326 A | 8/1989 | Stitt |
| 4,871,550 A | 10/1989 | Millman |
| 5,004,593 A | 4/1991 | Ames et al. |
| 5,236,899 A | 8/1993 | Durette |
| 5,397,778 A | 3/1995 | Forse et al. |
| 5,545,667 A | 8/1996 | Wiersema et al. |
| 5,654,337 A | 8/1997 | Roentsch et al. |
| 5,674,853 A | 10/1997 | Forse et al. |
| 5,739,107 A | 4/1998 | Cohen et al. |
| 5,753,211 A | 5/1998 | Garson et al. |
| 5,753,296 A | 5/1998 | Girsh |
| 5,855,619 A | 1/1999 | Caplan et al. |
| 5,902,617 A | 5/1999 | Pabst |
| 5,904,924 A | 5/1999 | Gaynor et al. |
| 5,958,684 A | 9/1999 | Van Leeuwen et al. |
| 6,153,582 A | 11/2000 | Skelnik |
| 6,153,622 A | 11/2000 | Cameron et al. |
| 6,197,356 B1 | 3/2001 | Girsh |
| 6,479,059 B2 | 11/2002 | Montanari et al. |
| 6,596,689 B2 | 7/2003 | Misevic |
| 6,974,796 B1 | 12/2005 | Girsh |
| 7,147,882 B2 | 12/2006 | Girsh |
| 7,790,678 B1 | 9/2010 | Girsh |
| 8,119,596 B2 | 2/2012 | Girsh |
| 2002/0058065 A1 | 5/2002 | Guivarc'h et al. |
| 2004/0156886 A1 | 8/2004 | Kose |

(Continued)

FOREIGN PATENT DOCUMENTS

| | | |
|---|---|---|
| JP | 2001-97872 | 10/1991 |
| WO | WO 92/21752 | 12/1992 |
| WO | WO 97/10723 | 3/1997 |

OTHER PUBLICATIONS

U.S. Appl. No. 10/752,298, filed Jan. 5, 2004, now abandoned.

(Continued)

*Primary Examiner* — Chih-Min Kam
(74) *Attorney, Agent, or Firm* — Saliwanchik, Lloyd & Eisenschenk

(57) ABSTRACT

A composition for treating damaged tissue and promoting healthy tissue growth, healing and tissue regeneration, wherein the composition comprises an extracellular matrix compound, a surface-active lipid, one or more enantiomericaily pure L-amino acids or glycine, a hydrophilic surfactant with a high HLB, as well as vitamins, minerals or trace elements. Not only does it maintain good health, but the components are non-intrusive, bio-safe, non-coalescent and can mimic normally occurring stem-cells within a body. When applied to diseased tissues, the subject compositions can stimulate, facilitate, and accelerate protein synthesis for the regeneration of diseased organs and tissues. The healing efficacy of these tissue components gives us further appreciation of the protective action of human tissue over and above and other than the immune protective system or perhaps an integral component part of the immune system.

29 Claims, No Drawings

(56) References Cited

U.S. PATENT DOCUMENTS

| | | |
|---|---|---|
| 2005/0260181 A1 | 11/2005 | Girsh |
| 2006/0074051 A1 | 4/2006 | Girsh |
| 2007/0014904 A1 | 1/2007 | Girsh |
| 2007/0037777 A1 | 2/2007 | Girsh |
| 2007/0231402 A1 | 10/2007 | Girsh |

OTHER PUBLICATIONS

U.S. Appl. No. 10/752,298, filed Jan. 5, 2004, Girsh.
U.S. Appl. No. 10/868,697, filed Jun. 14, 2004, Girsh.
U.S. Appl. No. 10/868,697, filed Jun. 14, 2004, claims as filed and claims pending after Election filed Mar. 13, 2008.
Henschen, A. et al. "Covalent Structure of Fibrinogen" *Annals of New York Academy of Sciences*, 1983, pp. 28-43, vol. 408.
Wayman, K.I. et al. "Neurodevelopmental outcome of young children with extrahepatic biliary atresia 1 year after liver transplantation" *The Journal of Pediatrics*, Dec. 1977, pp. 894-898, vol. 131, No. 6.
Neocate Product Information Sheet, downloaded from www-shsweb.co.uk on Jul. 20, 2000, pp. 1-2.
Office Action dated Aug. 22, 2006 in U.S. Appl. No. 11/212,530, filed Aug. 26, 2005.
Office Action dated Apr. 12, 2007 in U.S. Appl. No. 11/212,530, filed Aug. 26, 2005.
Office Action dated May 21, 2008 in U.S. Appl. No. 11/212,530, filed Aug. 26, 2005.
Office Action dated Feb. 6, 2006 in U.S. Appl. No. 10/269,613, filed Oct. 11, 2002.
Office Action dated Jun. 9. 2005 in U.S. Appl. No 10/752,298, filed Jan. 5, 2004.
Office Action dated Jan. 19, 2006 in U.S. Appl. No. 10/752,298, filed Jan. 5, 2004.
Office Action dated Jun. 28, 2006 in U.S. Appl. No. 10/752,298, filed Jan. 5, 2004.
Office Action dated May 25, 2007 in U.S. Appl. No. 10/752,298, filed Jan. 5, 2004.
Office Action dated Feb. 13, 2008 in U.S. Appl. No. 10/752,298, filed Jan. 5, 2004.
Patt, H.M.et al. (1953) "Comparitive protective effect of cysteine against fat neutron and gamma irradiation in mice" *Proc. Soc. Exp. Biol. Med.* Oct;84(1):189-193.
Patt, H.M et al. (1950) "The effect of cysteine on the peripheral blood of he irradiated rat" *Blood* Aug;5(8):758-763.
Straube, R.I. et al. (1953) "Studies with cysteinamine and cysteine in x-irradiated animals" *Proc. Soc. Exp. Biol. Med*. Dec;84(3):702-704.
Patt, H.M. (1954) "Radiation effects on mammalian systems" *Annu. Rev. Physiol.* 16:51-80.
Patt, H.M. et al. (1953) "Radiation dose reduction by cysteine" *J. Cell Physiol.* Dec;42(3):327-341.
Patt, H.M. et al. (1952) "Effect of x-rays on thymocytes and its modification by cysteine" *Proc. Soc. Exp. Biol. Med.* May;80(1):92-97.
Patt, H.M. et al. (1950) "Further studies on modification of sensitivity to X-rays by cysteine" *Proc. Soc. Exp. Biol. Med.* Jan;73(1):18-21.
Konstantinova, M.M. et al. (1983) "The role of endogenous glutathione in the action of sulfur-containing radio-protectors" *Radiobiologiia* Nov-Dec:23(6):749-753.
Patt, H.M. et al. (1949) "Cysteine protection against x-irradiation" *Science* 10:213-214.
Hall, E.J. (1994) "The discovery of radioprotectors mechanism of action" In: *Chapter 11, Radiology for the Radiologist*, 4th Ed., J.B. Lippincott Co., Philadelphia, PA, pp. 183-189.
Product Insert. Intralipid 20%® a 20% I.V. Fat Emulsion (Rev Apr. 2000) Baxter Healthcare Corporation, Clintec Nutrition Division, Deerfield, IL 60015 USA.
Office Action dated Oct. 9, 2007 in U.S. Appl. No. 11/073,514, filed Mar. 7, 2005.
Melichar, V. et al."Nitrogen and fat balance studies and aminograms in low birth weight infants fed modified human bank milk" *Padiatrie und Padologie*, 1986; pp. 241-248, vol. 21, entire document with English summary.
Wattiaux, M.A. "19) Milk composition and nutritional value" Dair Essentials, Badcock Institute for International Dairy Rsearch and Development, University of Wisconsin-Madison, Sep. 26, 1997, entire document at web: Www.babcock.wisc.edu/downloads/de/19.ed.pdf.
Martin, R. et al. "Human milk is a source of lactic acid bacteria for the infant gut" *The Journal of Pediatrics*, Dec. 2003, vol. 143, pp. 754-758.
Brooker, B.E. "The epithelial cells and cell fragments in human milk" *Cell and Tissue Research*, 1980, pp. 321-332, vol. 210.
Guerin-Danan, C. et al. "Milk fermented with yogurt cultures and *Lactobacillus casei* compared with yougurt and gelled milk: influence on intestinal microflora in healthy infants" *Am. J. Clin. Nutr.*, 1998, pp. 111-117, vol. 67.
Meigs, E.B. et al. "The comparative composition of human milk and of cow's milk" *The Journal of Biological Chemistry*, 1913, pp. 147-168, vol. XVI, No. 1.
Office Action dated Feb. 21, 2008 in U.S. Appl. No. 11/501,380, filed Aug. 9, 2006.
Office Action dated Nov. 18, 2008 in U.S. Appl. No. 10/868,697, filed Jun. 14, 2004.
Office Action dated Jul. 1, 2008 in U.S. Appl. No. 11/073,514, filed Mar. 7, 2005.
Enig, M.G. "Fat and cholesterol in human milk" Wise Traditions in Food, Farming and the Healing Arts, a quarterly magazine of the Weston A. Price Foundation, Fall 2001, Dec. 31, 2001, pp. 1-3.
Office Action dated Jun. 6, 2008 in U.S. Appl. No. 10/868,697, filed Jun. 14, 2004.
Office Action dated Nov. 17, 2008 in U.S. Appl. No. 10/752,298, filed Jan. 5, 2004.
Campbell, J.K. et al. "Tomato Phytochemicals and Prostate Cancer Risk" *The Journal of Nutrition*, 2004, pp. 3486S-3492S, vol. 134.
Vanderhoof, J.A. "Probiotics: future directions" *The American Journal of Clinical Medicine*, 2001, pp. 1152S-1155S, vol. 73 (suppl).

COMPOSITION WITH ANTI-INFLAMMATORY, PROTEIN SYNTHESIZING, TREATMENT OF ENZYME DEFICIENCY, ACTIVATING GENETIC THERAPY AND ANTI-CANCER ACTIVITY AND METHODS OF USE

CROSS-REFERENCE TO RELATED APPLICATIONS

This application is a continuation of U.S. Ser. No. 12/872,648, filed Aug. 31, 2010, which is a continuation of U.S. Ser. No. 10/765,664, filed Jan. 26, 2004, now U.S. Pat. No. 7,790,678, which is a Continuation-in-Part of U.S. Ser. No. 10/752,298, filed Jan. 5, 2004, now abandoned, which claims the benefit of 60/437,939, filed Jan. 3, 2003. This application also a continuation of U.S. Ser. No. 10/765,664, filed Jan. 26, 2004, now U.S. Pat. No. 7,790,678, which claims the benefit of U.S. Ser. Nos. 60/442,278, filed Jan. 24, 2003; 60/447,779, filed Feb. 13, 2003; 60/448,003, filed Feb. 18, 2003; and 60/448,497, filed Feb. 19, 2003. U.S. Ser. No. 12/872,648 is a continuation of U.S. Ser. No. 10/765,664 (now U.S. Pat. No. 7,790,678), filed Jan. 26, 2004 which is a Continuation-in-Part of U.S. Ser. No. 09/639,859, filed Aug. 16, 2000, now U.S. Pat. No. 6,974,796, which claims the benefit of U.S. Ser. No. 60/149,338, filed Aug. 17, 1999. These applications are all hereby incorporated by reference in their entireties, including all figures, formulae, references and tables.

BACKGROUND OF INVENTION

In prior art, the treatment of disease centers around the position to "kill" as if we are trying to kill an infectious agent. This is exemplified by the discovery that platinum kills bacteria. Many of the leading cancer products of prior art are derivatives of platinum (or similar toxic products derived from the periodic table) such as but not limited to cis-platinum and carbo platinum.

It would be desirable to surmount the awesome challenges of disease treatment by restructuring diseased tissue with biochemical and biophysical components of normal tissue, which have the associated features of restructuring, healing and regeneration of organs and tissue to their normal status. This series of inventions mimic, in analog fashion, human tissue and thereby draws from normal molecular structured biochemicals with required biophysical function and from pharmacopoeia from major industrialized countries.

This has been so accomplished with results which include a therapeutic stem cell like composition which by simulating, accelerating and facilitating stem cell healing increases the tissue regeneration capacity of the patient's stem cells, thereby reversing diseases of great severity and complication. For example, organ failure can be reversed without resorting to such extreme measures of desperation and gravity, including organ transplant or tissue graft. As a result of this unique focus and sourcing the associated risks and objections of dependency upon the use of human tissue and human embryonic tissue is not required.

This inventor has observed that tissue has a self healing effect promoting tissue healing and tissue regeneration. Not only does it maintain good health but also it has been observed that the patient's blood is withdrawn from patients with a leg ulcer and the blood is then applied to the ulcer the blood is shown to have healing qualities. Cartilage placed in a wound also promotes and accelerates wound healing. The anabolic biochemical and biophysical essence and equivalence of tissue has been found in these embodiments to have the same healing and tissue regeneration pharmacologic qualities, when devoid of genetic DNA mismatch and other catabolic factors including the catabolic effects of microorganism overgrowth that lacks pro-biotic qualities. The healing efficacy of these tissue components gives us further appreciation of the protective action of human tissue over and above (and other than) the immune protective system or perhaps an integral component of the immune system.

The components are most effective when freely available to the metabolic stream and thereby overcome the disease producing debris of disease and crystal seeding effect obstructive and foreign to the metabolic stream. Mismatching is further assured by adherence to tissue equilibrium particularly applied here the hydrophilic/lipophilic balance HLB equilibrium. Therapeutically, through polar surface active lipid surfactants permits the tissue to maintain the unique required strata of alternation of hydrophilic with hydrophobic components such as lipids.

This strata is analog to the earth's strata exemplified by the hydrophobic nucleus surrounded by hydrophobic cytoplasm further surrounded by lipophilic cell membrane and the strata is finalized with a hydrophilic extracellular matrix. The same patterned alternate strata can be seen in the biomolecular macromolecules of proteins with the lipophilic central core derived primarily from the essential amino acids surrounded by the hydrophilic periphery of primarily nonessential amino acids further forming and attracting a clathrate cage of structured ordered non-random, non-liquid water accounting for the alpha helix or beta sheet folding and associated and dependent biologic structure and function.

It has been found in these embodiments that high HLB surfactant treatment alters the allergenicity of cat protein's 3-D structure and pathogenicity.

These same biophysical features provide the opportunity to use highly hydrophilic surfactants with their high surfactant packing parameters to provide, through hydrogen bonding, a clathrate cage of structured water and energy input and change in entropy that enhances refolding of the misfolded proteins and protein derangements and aggregates that are pathophysiologic and pathogenetic basis for diseases such as Alzheimer's disease, Parkinson's disease, Mad Cow disease and its human equivalent transmissible spongiform encephalopathy. It is this tissue essence and this biochemical and biophysical molecular engineering that has resulted in therapeutic efficacy combined with bio-safety offering therapeutic opportunities that have been otherwise not forthcoming.

The prior art teaches a passive relationship, between the genetic code and amino acid structures. However, the prior art does not teach the use of therapeutic compositions for actively enhancing and normalizing functional aspects of the cell nucleus and cytoplasm in disease to stimulate, facilitate, and accelerate protein synthesis in diseased organs and tissues.

Therapeutic stimulant, activator and substrate compositions that provide therapy for hereditary diseases and conditions of hereditary pre-disposition were disclosed in provisional Patent Application Ser. No. 60/149,338, filed Aug. 17, 1999 and are described in co-pending, U.S. patent application Ser. No. 10/269,613, filed Oct. 11, 2002 (each of which is hereby incorporated by reference in their entireties). As there disclosed, molecular monomers having alpha amino- and alpha carboxylic groupings similar in molar ratio of the component amino acid monomers in human tissue and in accordance with the specific code of the 20 amino acids of human tissue can be used for the treatment of diseases.

This unique drug discovery technology and characteristics of therapeutic synthetic stem cell-like composition is unique to the prior art is a healing tissue regenerative therapy and has been shown to be effective in averting organ graft in the replacement of disease ravaged tissue whether inflammatory, acute, chronically inflammatory, degenerative, neoplastic or genetic pathogenesis or etiologic on the basis of mimicking and analog model of human and mammalian tissue. This anabolic tissue copy basis is not only a biochemical copy, but also a functional bio-physical model copy of normal tissue function, with meticulous avoidance of catabolic components, derived from a unique biologic periodic table. The subject composition also permits reorganization as if the disease were analog to a "bankruptcy" major deficiency with replenishment not only of the tissue, but even of its trace elements, vitamins and minerals. Additionally the diseased organ or tissue secretions also represent a biochemical and biophysical copy for therapeutic normalization of these secretions.

In producing these copies we have also copied the fluidity of function by mimicking and preparing an analog copy and therefore normalizing the hydrophilic lipophilic (HLB) equilibrium balance, with HLB (with intramolecular OH2/CH2 ratio of these embodiments exemplified by intramolecular composition Tween 80) surfactant energy input and associated change in entropy along with any defective human and mammalian tissue equilibria.

In so doing, not only the tissues, cells but even the microscopic and sub-microscopic structure and functions of the cell organelles undergo normalization of mitosis and apoptosis ideally characterized for anticancer therapy. The further normalization of mitosis includes the mitotic organizing centers of centrioles, peri-centriolar clouds, spindles, chromosomes and centromeres (kinetochores) of the chromosomes, acting like seeds of crystallization in conjunction with the microtubules and associated protein with tubulin tread milling polymerization. The mitotic associated tubulin protein of the microtubule has a double origin, the centriolar poles and the chromosome.

This nanogram and picogram pursuit of repair is all based on the atomic and molecular level of human tissue function as illustrated by Component #1, #2, #3, #4, and #5 of the composition of the subject invention.

We find sequential to the foregoing a bio-computer signaling system based on the semi-conductivity bio-computer inter-molecular, therefore intercellular and inter-tissue signaling system of all components of #1 and #2 and some components of #3. The functional biophysical overlapping of these three components is the polar surface active lipid surfactant intrinsic to these foregoing components of an emulsifier the expansion of biochemical surface area interaction by surfactant packing parameters and emulsion system, and most importantly thereby a control of fluidity, metabolic fluidity, metabolism electrochemical charge buildup and enhancement and signaling based on common semiconductor bio computer functionality and obviating, correcting, avoiding crossroads of disease. ECM Component #3 offers the proteoglycans complex aggregate to support the colloidal system with similar architectural structural support of structured water, viscosity and lubricant effect of the synovial membrane joints and vitreous helping to hold the respective retina and umbilical blood vessels in place and unobstructed analog to the cell membrane phospholipids of component #2, with hyaluronidase serving as a "colloidifier" analog to a high HLB emulsifier to adjust or reduce and "thin" viscosity to enhance flow.

This fluidizing effect converts roadblocks of disease such as crystals of calcium, cholesterol, uric acid, pigment, disease debris and exogenous crystals such as, but not limited to, silica and asbestos, all acting as disease producing microscopic shards or 'thorns' sticking in the metabolic throat and sides of the patient's tissue.

The anti-inflammatory effects associated with all three anti-inflammatory bio physiologic activities and accompany protein synthesis of components one and two (such as lysolecithin protein synthesis stimulus effects of PC of component two) as but not limited to the contrasting tetrahedral alpha amino acid non D, Levorotary amino acids and non-chiral glycine with proteins tissue fits with these tissue specific to the genetic code amino acids in sharp contrast to the aromatic benzene ring derivatives that do not fit with other inflammatory drugs and therefore also interfere with protein synthesis. Medication side effects are less when co-used with subject composition. Enhancement of enzymatic activity associated with surfactant packing parameters and companion increase in vital zeta potential with use of high HLB surfactants.

The foregoing can be exemplified by non-intrusive, biosafe, non-coalescent compositions comprise component #1, anabolic-non-dextrorotary ("non-D" L amino acids, including but not limited to L-amino acids and non-chiral glycine); component #2 (one or more cell membrane components formed by self-vesiculating surface-active polar lipids such as but not limited to phosphatidyl choline (PC) that forms the double layer of the mammalian cell and nuclear membranes), and component #3 (extracellular matrix material such as collagen, proteoglycans, chondroitin sulfate, or mixtures thereof).

These therapeutic compositions are abundantly supplied and are formulated to contain amino acids in amounts that correspond to molar ratio of amino acids in a damaged organ, tissue, or protein. The amounts of each component can be adjusted to match the nature of the organ or tissue being treated. In reversing disease through this series of inventions, major side effects can be greatly minimized with co-use or sole use with these therapeutic compositions.

It is not only in the applied biochemistry and its associated biomolecular structures but also the biophysical surfactant functions including surfactant packing parameters and particle charge of these three component compartments and particularly the key to this fluid dynamics fluidizing and hydrophilizing at code of osophical therapy (also present in components one and three with the most concentrated surfactant function in two) can be poignantly modulated even with the challenge of modulating and thereby normalizing the abnormal mitosis of cancer through the biophysical function and structure of the polar surface active lipids in component number two along with maturation factor of ethylene oxide Tween 80 component never two. The amount of surface-active polar lipid to include in the composition can be determined by viscosity measurements. Tissue concentration can be measured by viscosity (as used in blood serum which normally is 1.12 to 1.22 centipoise with upper limit of three). In the case of the intermediate HLB 8 to 11 (as exemplified by PC phosphatidyl choline when so used) circulation is improved 25% however there is no change in viscosity or the red blood cell sedimentation rate at these HLB ranges because of the fact that biophysical functional effects is upon the cell membrane. With its use the red cell membrane becomes more plastic, and is made more pliable thereby enhancing circulation and oxygenation.

Providing a polar surface active lipid liquid crystal surfactant of extreme HLB to overcome the disturbed fluid balance and lack of fluidity of the biophysical inertia of the non metabolizable necrotic debris of the disease process results in a crystal (such as but not limited to calcium phosphate crystal where the phosphorylase enzyme which in turn releases phosphate to produce the insoluble salt deposit of calcium phosphate).

MRI crystalline calcium salts detected by MRI in the coronary artery may make stress testing not necessary. And biochemical models so derived from the crystallization requirements (as historically in the case out of the x-ray diffraction study of the DNA molecule) may lead to the biomolecular engineering model of life but the possibility of the disease variant of life (in contrast to normal model of life) must be given serious contrasting consideration.

Other intracellular and tissue body deposition responses include the lipid cholesterol crystal found in atherosclerosis and coronary artery disease whereby the lipid crystal has a melting point of 50 degrees higher than normal body temperature. Other crystal responses included poorly soluble uric acid crystal deposits derived from purine metabolic products or exogenous derived silica crystal and asbestos bodies and other difficult to process shards resistant to fluidity necessary for normal metabolic processing. These perpetuating foreign substances promote chronic inflammation, chronic granulomatous reactions, and in certain situations (such as but not limited to asbestos) may progress to cancer after a long period of deposition (which may be as long as 20 years). In this debris may included poorly attainable or derivable processing due to lack of metabolic tools (such as but not limited to in the case of a carbohydrate and glycogen trapped as polymerized glucose form of energy not obtainable from glucose because of the lack of insulin receptor response as in the case of Type II diabetes or deficiency of enzymes as in the case of "storage diseases"). In the case of trans fats, it has been observed to be associated with Type II diabetes with poor insulin receptor response even though production of insulin is adequate. Hereto it is likely that trans fat deposits, without adaptable trans fat enzymes, and again with 40 to 50 degrees melting point higher than body temperature may be amenable to disbursement of the fat with low HLB surfactant followed by further fluidizing the fat with the high HLB surfactant.

Protein, when misfolded, loses its biologic function in diseases such as Alzheimer's disease, Huntington's disease, and Mad Cow disease with resulting neuropathologic response of tangles, which also may be seen with lead poisoning and metals such as aluminum and zinc that are under consideration for their involvement with Alzheimer's disease.

The extracellular matrix material of Component #3 can include, in addition to collagen and elastin, cartilage derived from tracheal rings (of bovine or shark origin) and complex aggregates of very large macromolecule straight chain amino polysaccharide hyaluronic acid polymers of glucosamine and glucuronic acid covalently linked to (proteins and core proteins) and non-covalently linked to chondroitin sulfate.

The function of these extracellular matrix compounds include architectural integrity, imbibing of water as a biocolloid, serving as a lubricated surface (as exemplified by the synovial membranes and rationale for a therapeutic application in regard to arthritis) and maintenance of viscosity analog to component number two the polar surface active lipids such as but not limited to phosphatidylcholine with an HLB of 10 to 11. Hyaluronidase has been looked upon in the body and therapeutically as a fluidizing, viscosity reducing, thinning enzyme with analog effect of high HLB (15 to 20) surfactants (such as but not limited to Tween 80 and sodium lauryl sulfate).

A 48 percent inhibition of calcium oxalate urinary tract stone formation was observed in a multi-center study of more than 120 patients given glycoaminoglycans sulfated polysaccharide. The remaining patients formed stones that were smaller and more readily removable in regard to crystal cell adhesion. Similar effects with ECM on blood rheology was noted as with extreme of HLB response with reduction of blood viscosity and lipids as well as anti-coagulant effects.

In other multi-center studies more than 100 patients showed significant improvement in wound healing with a 48% increase in tensile strength of healed wound. Similar effects were noted in controlled animal studies.

Optional components for the compositions of the subject invention, include, but are not limited to, non-hydrolysate-derived milk substitutes (free of catabolic products and D amino acids such as microorganism, derived sources). When used in patients with clinically suspected milk allergy or bronchial asthma respiratory tract allergy (such as nasal allergy and hay fever (documentation with allergy skin testing is usually nonproductive)), the patients respond to this therapeutic composition, which may in terms of therapeutic rationale and mechanism response, most probably reside in the anti-inflammatory action, immune modulatory effects completely free of side effects such as commonly seen soporific effects of the antihistamines used for allergic rhinitis, or the side effects of antiasthmatic sympathomimetics and corticosteroids. Also as stressed when used in conjunction with these anti-asthmatic, anti-allergic medications side effects are greatly minimized. This is exemplified by the avoidance of common soporific side effects seen with antihistaminics. As with all these therapeutic applications, their co-use with medications lessens the dosage and the associated side effects.

Catabolic products are avoided or absent from the compositions, especially chiral amino acids and racemic mixtures containing amino acids in D form, as well as, e.g., cyclosporin oligopeptides and bacterial cellular walls. More severe complications of allergic and hypersensitivity diseases may include autoimmune disease such as lupus erythematosis and medication reaction induced false lupus. False lupus has responded to these therapeutic compositions including the collagen proteoglycan aggregate cartilage, chondroitin sulfate complex, thereby avoiding the risks of cortico-steroids, commonly required in these patients, particularly in those patients with the complication of pericardial infusion.

The compositions can also optionally incorporate material that includes stem cells or materials derived from after-birth tissue such as placenta and umbilical cord. The compositions can also include materials that correspond in amino acid composition to mother's milk or to other materials encountered during fetal and infantile development.

The compositions of the invention also mimic mother's milk or embryonal tissue. This embryonal tissue simultaneously mimics healing tissue, associated with such diseases as inflammation and tissue damage such as trauma, at the same time mimicking and being analogous to mammalian and particularly the human stem cell.

In addition, vitamin D supplied in this therapeutic stem cell subject composition and the case in toxic heavy metals would drive and sequester these heavy metals such as not limited to lead into the bones by their chelating; effects thereby greatly minimizing their neurologic to toxic effects.

Additionally, vitamin D can optionally be added to further direct this enzyme therapy to the bone marrow involved in lysosomal storage disease encroachment on the bone marrow. If therapeutic replacement enzymes are not available, high HLB surfactant such as but not limited to Tween 80 or sodium lauryl sulfate 0.125% to 1% or 10% to 50% of the LD 50 in normal animals with normal HLBs.

In this therapeutic composition can further comprise phosphatidylcholine (PC), commonly derived from the soybean plant by degumming followed by acetone extraction. The highest concentrations of PC are present at birth during youth and young adult phases of life and then decreases progressively until old age. Premature infants are particularly prone to atelectasis or lung collapse, respiratory distress syndrome of the newborn and may be contrasted with full term infants that have adequate PC levels. The sudden rise in saturated PC at 34 to 36 weeks of gestation marks the development of fetal lung maturity. The phospholipids produced represent most of the lipid produced the majority of which is lecithin-saturated PC up to 85 percent of the lecithin, 60 percent of the lecithin is dipalmitoyl PC. Other lipids present are phosphatidylglycerol (PG), phosphatidylinositol (PI), phosphatidylethanolamine (PE).

Plant hormones, such as but not limited to, ethylene, abscisic acid (ABA), and gibberelic acid (GA3), a gibberelin, zeatin a (cytokine), auxins (indole-3 acetic acid, IAA) involved in chemiosmotic proton gradients, Zeatin (a cytokine) may be offered in the subject compositions for the prevention or reduction of premature births. The plant hormones may be added to highly hydrophilic surfactants in the modulation of mitosis adding to the management of cancer, and may be incorporated in therapeutic stem cell-like subject compositions, all with a high degree of bio-safety. This is also emphasized relating to other embodiments concerning modulation of mitosis.

Variants of Tween 80, a highly ethoxylated high HLB hydrophilic surfactant with 20 moles of ethylene oxide, can be ethoxylated further with 20-40 or more moles of ethylene oxide to increase the HLB. Obversely Myrj represents a low HLB surfactant with 8 moles of ethylene oxide moles to 1 mole of fatty acid such as stearic acid. Two carbon ethylene, (and multiplicity of ethylene oxide derived surfactants), function as a maturation factor, and may be combined with hydrophilic surfactant activity in these ethoxylated surfactants.

The compositions can be employed for local and systemic therapies and can be delivered by topical, oral, parenteral or intravenous routes. In the case of cancer, intralesional or even intra-arterially administration may be practiced. A more preferred route is oral administration, preferably by oral mucosal delivery in which the compositions are formulated into a lozenge or gum that is brought into contact with the oral buccal sublingual, or pharyngeal mucosal surface for a few to twenty minutes (or longer) until absorbed. The high HLB mediated oral mucosal delivery system is as efficacious as parenteral administration of such medications and prophylactic agents as vaccines (further documented by laboratory measured response in other embodiments). When an oral route of administration is used, the component concentrations can be lower than in intravenous routes, since the components do not pass through the liver. This oral mucosal delivery system can also be advantageously used with enzymes or hormones administration. The therapeutic compositions are preferably administered at a temperature slightly less than 100 degrees F., more preferably at or about 98.6 degrees F., to further enhance the synergism of, surfactant and enzymatic activity.

The compositions offer protective effect including but not limited to the chelating protective elect of the macromolecules such as, but not limited to, DNA and their protection from toxic chemicals such as heavy metals as well as antioxidant protection from radiation. The exemplary antioxidants for optional addition to the subject compositions include, but are not limited to vitamin A in the form of beta-carotene, 10,000 units per day; D-alpha tocopherol 400 units ideally chelated 200 micrograms of selenium to the methionine per day; and/or ascorbic acid preferably in capsule form 500 milligrams to 8 g (particularly when uric acid levels are elevated and functioning as a natural antioxidant), in divided dosages. The effects of the compositions can be long-lasting, with benefits extending for six months or more after therapy is discontinued.

The pharmacodynamic basis for successful unexpected therapeutic results with the compositions of the invention include (a) hydrogen bonding, (b) anionic charge, (c) electrostatic polar forces, (d) van der Waal forces, and (e) zeta potential associated with the non-covalent interactions with the macromolecules.

In addition to having anti-inflammatory and tissue healing activities, the compositions provide a biochemical environment in accord with the law of mass action that can activate inactive genomic components and increase expression of one-third or more of the genome thereby potentially countering disease including hereditary conditions. This can counter a genetic imbalance and can therefore overwhelm disease-producing genes, even those produced by hereditary changes.

In addition the pharmacodynamic basis for the effects of genetic therapy non-chiral function in a self-perpetuating mode through the L tetrahedral 3D fit of L-amino acids and glycine non-covalent biochemical macromolecular binding to D polysaccharides such as but not limited to the genetic system macromolecules DNA, RNA, ribosomal RNA and ribosomes and their respective polymerases furthered by the law of mass action mediated by progressive therapy with synthetic therapeutic stem cell-like subject composition of L-amino acid and glycine. Thereby, in addition, these pharmacodynamic effects of genetic therapy function in a self-perpetuating mode through the biochemical law of mass action mediated by progressive therapy with synthetic therapeutic tissue and stem cell-like subject composition of L-amino acid and glycine, polar surface-active lipids and optional inclusion of extracellular matrix scaffold.

L-tetrahedral fit; Surfaces and Tetrahedral fit of each alpha amino acid. Surface magnification of molar ration (protein) and reactive moieties and tetrahedral fit in protein synthesis and as therapeutic anti-inflammatory healing therapy.

The C2 through C6 twenty L amino acids and non chiral glycine including the 8 C3 propionic acid derivatives are analog to such C3 propionic acid derivative, and Ca4 3butyric acid derivative, anti-inflammatory medications and their reactive moieties. In contrast the routine anti-inflammatories listed in the PDR are benzene ring containing compounds from which many medications and anti-inflammatory drugs are derived, lacking the L alpha amino acid and glycine 3D tetrahedron fit in protein synthesis, actually interfere with protein synthesis, (a non-tetrahedral 3D planar gliding action is present in anti-inflammatory medication).

The compositions can also be employed for metabolic diseases and conditions such as Type 1 with insulin deficiency wherein the molar ratio of the protein insulin may be incorporated into subject composition to stimulate the production of insulin as well as replacing suspected trace element deficiency such as but not limited to chromium or type if diabetes and the diabetic state where there is adequate insulin but with inadequate insulin receptor response which may be modified with high HLB therapy.

The therapeutic compositions may also be specifically applied to addiction by mimicking normal tissue metabolism and normal tissue including the L-amino acid glycine molar ratio of endorphin to metabolically stimulate and in fact coerce the body to produce this hormone. These same principles and therapeutic components have been applied in normalizing, as noted in a prior embodiment's dependency or withdrawal symptoms such as, but not limited to, the use of drugs in controlled substances, alcohol and/or drug and tobacco addiction in the medical patient or veterinary practice or experimental conditions such as the animal or tissue culture. Therefore these compositions form a clinical bridge beyond other advanced technologies that have not to date found a clinical application. Examples of suitable therapeutic uses include the treatment of Crohn's Disease, and in particular Pediatric Crohn's Disease (PCD), a chronic, relapsing, unremitting disease with grave, guarded prognosis for which conventional treatment includes high-risk immune suppressants such as corticosteroids at high doses. In many cases, particularly in pediatric cases, major surgical intervention is required within five (5) years of initiation of observation, with resection of up to several hundred grams of diseased organ tissue. Surgical intervention effectively arrests disease complications but has no effect on the clinical course of the disease. In fact, many patients require repeated surgical intervention. The use of these therapeutic stem cell-like subject compositions reduces or eliminates long-term corticosteroid use in these patients along with reducing side effects including but not limited to the interference and prevention of healing (so important in the management of Crohn's disease or Pediatric Crohn's disease) in these patients.

When these tissue normalizing principles and therapeutic subject compositions have been used in allergic asthmatic disease, therapeutic benefits have included: minimizing emergency use of corticosteroids, or possibly excluding the need for bronchodilator medication effect of sympathomimetic medication such as the beta sympathomimetic agonists. Further minimizing emergency use of sympathomimetic medications and their vicious cycle, of rhinitis medicamodosa or asthmatic bronchitis or potential bronchopulmonary equivalent asthmatic medicamentosa side effects seen with the past inhalation overuse of isoproterenol as the locked lung syndrome.

Additionally, transplantation or other surgery can be averted in congenital biliary atresia (CBA), a disease that is usually fatal if left untreated surgically. Even though CBA has an incidence of 300 cases occurring annually in the U.S. this disease represents the most common rational for liver transplantation in the pediatric age group.

The co-use of subject composition with the many medications available and prescribed from the PDR extend synergistic pharmacodynamics of these subject compositions and may be integrated with the successful bio-efficacy of the therapeutic effects of the compositions, exemplified by:

(1) reinstitution of organ and tissue function regardless of organ and tissue involved and regardless of etiology, such as but not limited to trauma;

(2) diseases of inherited predisposition such as, but not limited to, lysosomal storage diseases and deficiency diseases such as but not limited to enzymatic deficiency including for example, lysosomal storage disease in addition to specific enzyme deficiency replacement, residual tissue and organ dysfunction due to encroachment of distended lysosomes may be further treated with these subject compositions. This includes HLB modulation with the added advantage of the polar surface active lipid surfactant high HLB packing parameter to synergize, facilitate and accelerate small amounts of enzyme that may be present. This is accomplished by increasing surface area, not only of the deficient enzyme, but also of its substrate to maximize the enzyme's metabolic activity. By these methods, the genetic profile and pattern predisposing to disease in treatment will be minimized and normal genetic function become more dominant. Include as exemplified here but not limited to even the recessive lysosomal storage diseases.

Diseases and the syndrome of diseases may be viewed here as being analog to an insoluble crystalline 'thorn in the side' of the patient's tissue and metabolic processes whether diseases such as obesity with insoluble fat particles, atherosclerosis with cholesterol crystals, cancer, genetic diseases lacking enzymes to fluidize and hydrophilize these lysosomal deposits, or other insoluble crystal like structures such as asbestos or silicosis. The liquid crystals provided in this discovery characteristic of the polar surface active lipids thereby reverses these disease mechanisms structures and functions whether by the highly hydrophilic polar surface active lipid surfactant and or by the initial in component dispersed at other fat bite highly lipophilic polar surface active lipid surfactant.

The added advantage offered by these surfactants is that by making these crystalline or crystalline like non-soluble metabolites randomly disbursed thereby changing entropy, energy is also provided at the same time equivalent to energy of metabolizing and fat such as palmitic acid or the combustion of paper with the release of energy to complete the metabolism of these disease causing crystalline structures.

Current medication in the public domain emphasizes the use of (as exemplified in cancer) of platinum and cis-platinum and other allied anti-cancer therapeutic agents. These agents were originally noted to be lethal to infectious microorganisms and this concept and was further translated to the therapy of cancer.

Singular and novel to the prior art is therapy for infectious disease or for cancer that is not dependent on its lethality to tissue and its associated disease but is dependent upon the principle that human tissue can be facilitated and synergized to assume the function and structure of replicating itself, thereby replacing the vicious cycle of disease. This averts major side effects difficult to accept that are associated with therapeutic lethality concept, thereby normalizing human tissue using compositions that mimic and are analog to human tissue not only in structure but also in function.

Such compositions can be used to treat neoplasms as in cancer or infectious diseases, in overcoming antibiotic sensitivity, or inactivation without damaging or killing human tissue. In the case of infectious disease, the same high HLB polar surface active lipid surfactant composition as in the anti-cancer therapeutic components as in #2 (which may be used alone or in concert with synthetic stem cell containing and compositions #1, 2, and 3) are used to counter such microorganism invasive modalities as lipid A, LPS (lipopolysaccharide as in toxic shock syndrome) that were formerly antibiotic resistant. A similar dual mechanism as with platinum however without major side effect concerns.

In inflammation and degenerative diseases without giving up imperative protein synthesis in healing associated with the existing anti-inflammatory drugs, synthetic therapeutic stem cell containing compositions #1, #2, and #3 can be used.

Congenital and genetic diseases can be treated using a composition of a "synthetic stem cell" containing therapeutic compositions #1, #2, and #3 without assuming life threatening entree through the portal vein and infectious microorganism carrier agents. For example, oral mucosal administration can be used, (thereby bypassing portal vein delivery) in these so targeted applications.

Trauma management can be performed with the local and systemic use of a synthetic stem cell composition containing compositions #1, #2 and #3, while greatly minimizing additional trauma and salvaging tissue by minimizing the requirement of debriedment. This provides a sutureless wound closure using progressive approximations with steri strips and inactivation of collagenase which has been activated by cortico-steroids, (which has become more commonly used in the management of chronic diseases).

These foregoing treatments combined as one therapeutic unit but administered as a single dosage or two to 4 times daily divided dosages may be given locally, systemically including intravenous administration and oral mucosal delivery system companion to this series of inventions.

SUMMARY OF THE INVENTION

Compositions of the subject invention can comprise three, four, or five of the following components:

Component #1: 10 to 25 grams of molar ratio amino acids such as but not limited to Neocate (SHS, Liverpool, U.K.).

Furthered by the law of mass action coercing the protein assemblage system three to four times a day, L amino acids and glycine non-covalently bond and fit with the dextrorotary pentose macromolecules of the protein assemblage system's template DNA and RNA those messenger and transfer RNA and ribosomal macromolecules.

Component #2: Polar surface active lipid, Phosphatidylcholine (PC) 0.9 g administered one to three times daily, (American Lecithin, Oxford, Conn.) or available in component #1 in L Neocate; Phosphatidylserine (PS) 100 mg contained in a 500 mg complex capsule administered 1 to 3 times daily, (Serinaid, Springfield, Utah); anti-inflammatory Omega 3 fatty acids, 1000 mg per 2 capsules, 2 capsules two to three times daily; 100 mg D-alpha tocopherol antioxidant, antirancidity fish oil complex, with active ingredients 180 mg EPA, 125 mg DHA and/or seed oil flaxseed oil (250 mg, organically grown replacing 100 mg of DHA). High HLB polar surface active lipid surfactants such as Tween 80, may be used alone or with Components #1, #2, and #3 for: (a) modulation of mitosis (>normal), as a normal progression; or (b) normalizing mitosis of cancer.

In cancer with the therapeutic use of highly hydrophilic surfactant such as Tween 80 with its hexagonal geometric format microscopically analog to normal mitosis, as shown in other embodiments may now be used to fluidize and normalize to the normal metaphase and anaphase stages of mitosis to progress to 2 normal daughter cells instead of being arrested or 'stuck', in an analog fashion as an old phonographic record might be stuck at the mitosis organization center MOTC at which site and transitional time a crystallization like seeding in the growth of crystals effect occurs with regard to the tread milling polymerization of tubulin and microtubulin with new tubulin molecules added at the growing advancing end of the microtubules whereas others are lost in depolymerization at the opposite microtubulin end (at anaphase depolymerization at this end of the microtubules occurs) until the analog player needle is advanced or normalized as in the case of cancer with high HLB surfactants. This high HLB anticancer activity has been shown in foregoing and in prior embodiments.

This normal function of normal progression of mitosis may be further envisioned as clasped hands which progressively separate at metaphase and the fingers of the clasp hands completely separate and endow each daughter cell with the equal quantitative and qualitative complement of DNA to continue their genetic activity. A maturation factor is also contained in the same Tween 80 molecule in the form of ethylene oxide (20 moles), resulting in normal progression resulting in apoptosis followed by new cellular regeneration. The hydrophilicity is further increased not only by the 20 oxygen atoms as OH2 in the 20 moles of ethylene oxide and six atoms of oxygen in the one mole of sorbitol but also by the central double-bond of one mole of oleic acid interrupting the 17 consecutive CH2 found in the more hydrophobic stearic acid as an analog "elbow" joint (c). Reduction in abnormal mitosis and cancer cells, approximately 50% histopathologically, after Tween 80, 0.125% of exposure after 24-48 hours, as well as 76% to 83% cancer cell inactivation in vitro breast cancer tissue culture monitored by inactivation of cancer cell mitochondria, (d) progression of cellular maturation resulting in apoptosis with ethylene oxide, a maturation and ripening factor for fruit in agriculture (an analog structural function in cell physiology not taught in the prior art), a monomer of Tween 80 which contains 20 moles of ethylene oxide.

All of the surfactants may be used as the equivalent weight volume dosage as the 0.125 percent dosage in these embodiments. Or they may be used with a therapeutic dosage of 10 to 20 to 50% of the LD 50, for example Tween 80 (with a dosage of 20 to 50% of the LD 50) LD 50 in the experimental animals (rats and mice) is 7.5 ml per kilogram (identical to highly lipophilic surfactant PGPR) with a Tween 80 or PGPR dosage of 10 to 50% of the LD 50, in a 70 kilogram patient the starting total daily dosage would be 50 to 100 ml, further divided into three to four dosages daily. It must be noted that the LD 50 is based upon studies in normal animals with normal hydrophilic/lipophilic equilibrium balance HLB. This specialized use is for patients with abnormal HLB requiring significant hydrophilic surfactant dosage. Therefore this latitude expanding the dosage in these patients is therapeutic in contrast to the LD 50 studies of normal HLB animals that did not require HLB modulation. The LD 50 for sodium lauryl sulfate 1288 mg per kilogram in the experimental animal, (rats orally) with or 900 to 1800 mg, further divided into three to four dosages daily Tween 80. Low HLB polar surface active lipid lipophilic surfactant PGPR polyglycerol polyricinolate 0.3% mother range of 0.01 to 0.05% to 10% may be used in any of these applications as a thrust mechanism to disperse and mobilize the hydrophobic tissue components at 4 to 12 hours before use of foregoing of high HLB surfactant.

Antioxidants such as D-alpha tocopherol 400 units, ascorbic acid 500-1000 milligrams spansule, beta-carotene 10,000 units, along with the L amino acid glycine of this therapeutic composition giving non-covalent DNA macromolecular protection also helpful in this anti-cancer therapeutic application of subject composition.

Component #3: The extracellular matrix can be given in the form of 740 mg capsules, 4 to 6 capsules 3 times daily. The capsules comprise a proteoglycan aggregate complex of cartilage, chondroitin sulfate covalently bonded to core proteins, further non-covalently linked to macro molecule of hyaluronic acid and collagen (see for example, Cartilade, Bio-Therapies, Inc., Fairfield, N.J.). Component #3 is therapeutically used along with component #2 self-vesiculating phosphatidylcholine with HLB of 10 to 11 and will further protect the cell and tissue.

This therapeutic formulation will further protect from radiation damage as in radiation therapy of cancer and/or radiation in regard to bio-terrorism attacks and nuclear plant accidents and in this protective function joins component #1 in radioprotection. Observations regarding amino acid amino groups and SH groups of cysteine should not exceed 1 g per day, however in the case of cancer, larger dosages to be considered such as 1 to 2 grams daily, indicate that the SH group is further protected by other phosphate groups as in phosphatidylcholine of component #2, or by the addition of adenosine diphosphate with the effect of promoting differentiation so important in countering the most aggressive anaplastic aspects of cancer. CSF cytostatic factor may also be added synergistically to compositions for this anti-cancer therapy. This may be derived from the cytoplasmic sap of the unfertilized egg and has similar differentiation promotion factors that are anti-cancer. This unfertilized egg CSF cytostatic, cytoplasmic factor may be sourced and derived from any unfertilized ovum including fish eggs, including sourcing as low allergenic risk potential frogs and/or ostrich eggs since derived from a source where exposure and sensitization has not (or only rarely) occurred.

The compositions offer protective effects including but not limited to the chelating protective effect for macromolecules including but not limited to DNA and their protection from toxic chemicals such as heavy metals as well as antioxidant protection from radiation. The optional addition of antioxidants, such as but not limited to vitamin A (in the form of beta-carotene 10,000 units per day) D-alpha tocopherol, 400 units, ideally chelated to 200 micrograms of selenium to the methionine, per day, ascorbic acid preferably in capsule form 500 milligrams to 8 g in divided dosages is also contemplated by the subject invention.

The inter-biochemical radio-protection of these components of synthetic stem cell therapeutic composition is analog to the protection of aminophostine without the very sickening side effects of nausea and vomiting of aminophostine which may be further minimized (as the case in optional co-use with any therapy with major side effects) by this synthetic stem cell therapeutic subject composition when these three #1 components and specific dosages of subject composition are used.

Further to the use of the extra cellular matrix component #3 for the management of cancer the addition of ECM component #3 helps to (1) complete the copy of human tissue; (2) it also adds 50% additional healing capacity to a wound or disease; and (3) it is of great value in correcting the healing deficiency of many patients requiring corticosteroid therapy.

An anabolic medicament is also provided which is involved in tissue healing and tissue regenerative which along with mimicking the molar ratio of the 20 free non D-amino acids specified in the genetic code of human tissue protein. The composition also mimics all the other essential components of human tissue including the polar surface active lipid phospholipids, such as phosphatidylcholine, omega-3 fatty acid essential fats, as well as the extracellular matrix composition comprising: (1) fibrous structural proteins such as collagen and elastin, (2) adhesive glycoproteins such as laminin and fibronectin, and (3) proteoglycans and hyaluronan consisting of a core protein and polymers of aminated disaccharides which are also sulfated polysaccharides and glycosylated proteins (glycoproteins).

The sulfated polysaccharides include, but not limited to, chondroitin sulfate and proteoglycan complexes of cartilage wherein chondroitin sulfate is covalently linked to extended core protein molecules which in turn are non-covalently linked to a huge hyaluronic acid polysaccharide glycosaminoglycans polymer molecule with the aid of link proteins. The subject compositions also provide a therapeutic correction of the major complicating multiple metabolic component deficiencies to synergistically continue the therapeutic correction of diseases such as Crohn's disease and pediatric Crohn's disease and specifically in the management of regional ileitis characterizing Crohn's disease in that the ileum is normally the sole site of vitamin B12 absorption and uniquely here whose vitamin B12 levels are less than ten percent of normal: of statistical significance joining a less than ten percent of normal vitamin A level (retinol) correction which locally and systemically corrects healing deficiency in this disease associated with long-term steroids along with a less than ten percent vitamin D level, vitamin D, E (D-alpha tocopherol) and prothrombin time in contrast to less than 20% of normal levels of red cell folate, copper, less than 30% zinc, serum folate, plasma ascorbate, less than 50% plasma selenium and hemoglobin other trace elements and minerals and vitamins and enzyme study such as less than 90% serum and plasma glutathione peroxidase, ferritin of a total of 15 studied components due to the ravages of disease (such as but not limited to progressive severe gastrointestinal disease such as the chronic granulomatous inflammatory disease such as Crohn's disease which specifically in its pathogenesis targets the ileum and its associated negative nitrogen balance (primary to the disease per se and secondary to malabsorption and enzymatic deficiency and chronic recurrent severe diarrhea)) and even further complications which include therapeutic side effects such as but not limited to the side effects of corticosteroids which include growth retardation and interference with pubertal development.

Inclusive in this response of 450 patients collated as a multi-center study is in response to foregoing therapy and is further inclusive of a response to vitamin, mineral, and trace element replacement therapy. It may be looked upon therapeutically as mimicking these normal components and quantitative levels of vitamins and minerals and trace elements of human tissue.

Each disease group will be studied for deficiencies which will be corrected as exemplified by components #4 and #5 to complete the mimicking and analog structure of normal tissue in the normal replication of human tissue, normalizing its structure and function in order to bring about the arrest of the vicious cycle of diseases and their pathogenic mechanisms.

Component #4: The 4th component in helping to complete and attain mimicking and analog to normal human tissue comprises vitamins, minerals, and trace elements. Utilizing documented deficiencies of vitamins, minerals and trace elements from available studies or performing pilot study guide lines. Exemplary deficiencies in Crohn's disease are documented in the examples presented. Vitamins, minerals and trace elements can be provided in various concentrations. For example, vitamin B12 (100 micrograms), vitamin A (as beta-carotene 10,000 units), vitamin D, vitamin E, D-alpha tocopherol, Selenium 200 micrograms chelated with methionine as sodium selenomethionine (or to sulfur containing cysteine).

Component #5 comprises Phytozyme, (Life Plus Int'l, Batesville Ariz.), Amylase 50 mg., Bile 45 mg., Bromelain 30 mg., Lipase 25 mg., Pancreatin 6× (NF.) 100 mg., Pancrelipase 110 mg., Papain 30 mg., Pepsin 70 mg., Betaine HCl 100 mg., and Probiolic Blend 20 mg tablet.

Ingredients: Betaine, HCl, Pancrelipase, Pancreatin 6× (N.F.), Pepsin, Dicalcium Phosphate, Amylase, Bile, Bromelain, Papain, Lipase, L-Glutamic Acid, (ProBio Tx), Stabilized Probiotic Blend (Each dosage: 200,000,000 pro-biotic micro-flora including *Lactobacillus acidophilus* DDS-1, *Bifido-bacterium bifidum, Lactobacillus bulgaricus, Lactobacillus salivarius*), vegetable and fruit concentrates. Deficiencies of pancreatic enzymes are readily available in exampled disease, Crohn's disease, along with cystic fibrosis. Therefore corrected here in the therapeutic component formulations to normalize not only human tissue but its secretions. Reversal to normal flora with pro-biotic also readily available and, therefore, used here for the same therapeutic rationale of normalization of tissue, its symbiotic surface bacteria and associated secretion contents of enzymes.

This detailed therapeutic replication of normal human tissue secretions, deficient in such diseases as Crohn's disease and cystic fibrosis, (and therefore synergizes further complete reversal of disease tissue). By including therapeutic components #4 and #5 and secretions of the tissue and the normalization of the micro-organism flora with associated normalization of function of this gastrointestinal Crohn's diseased tissue has made possible for this patient for the first time to further reduce from one tablet of the corticosteroid that this three component therapy has permitted to use ½ tablet instead (Triamcinalone, generic) for the first time in three decades. The side effects this patient has sustained from long-term corticosteroids has been worsening of osteoporosis documented by two successive bone scans two years apart, recurrent bruising and failure to heal including two threats of the need for skin graft which this subject composition stem cell-like treatment has prevented.

Component #5: In the case of the gastrointestinal tract in diseases such as, but not limited to, Crohn's disease, the addition of enzymatic therapy of composition #5 and the addition of pancreatic and enzymatic replacement of deficiencies present herein normalizes the gastrointestinal secretion component and byproduct of human tissue. The addition of pro-biotic microorganism therapy such as, but not limited to, *Saccharomyces Boulardii* helps normalize the abnormal microflora that the disease gastrointestinal tract such as but not limited to Crohn's disease predisposes to thereby even further normalizing abnormal microflora (which this vicious cycle chronic granulomatous Crohn's disease has fostered) the gastrointestinal microflora, tissues and secretions.

An extension of treatment of the synthetic stem cell therapy subject composition in the same patient as Ex. 1 with the addition of component #4 presented in detail in Ser. No. 09/639,859 and Therapeutic component #5 enzyme and pro-biotic 0.9 g tablets two tablets daily to three times a day preferably before meals of enzyme replacement and pro-biotic microflora normalizing factor. These favorable conditions make it more and more difficult for the diseased tissue, such as but not limited to chronic granulomatous disease, as in Crohn's disease and thereby reversing the vicious cycle of this disease and other diseases such as but not limited to Crohn's disease. This has proved itself clinically in the embodiment example cited here wherein digestive enzyme formulation containing pancreatic enzyme replacement, (as well as bile which has also been incriminated as deficient in Crohn's disease) along with pro-biotic micro-organism resulted in flora normalization. The pro-biotic in this case was *Lactobacillus acidophilus, Bifidobacterium bifidum, Lactobacillus bulgaricus, Lactobacillus salivarius* use of in this addition and completion of the normalization therapeutic stem cell-like repair kit formulation.

Most importantly component steps are analogous to a team or corporate approach to the anabolic reconstructive reversal of the pathogenesis of a complex vicious cycled catabolic destructive disease further analog to the underlying pathogenetic mechanisms and the basis of the former refractory state of disease. Crohn's disease and many other diseases with such analogous pathogenetic destructive componential mechanisms, associated deficiencies and medication side effects can be treated with the subject composition. Preferably to best address this disease state, all components of synthetic stem cell like subject composition formulations are contained in the molar ratios of human tissue.

The human tissue normal molar ratios of these foregoing components include such as, but not limited to, non D-amino acids of the 20 amino acids specified in the human genetic code, polar surface active lipids such as, but not limited to, cell membrane components, extracellular matrix components, vitamins, minerals, trace elements are herein defined as being at least 90% of the composition by weight and 10% by weight or less of composition that is not in conformance with the molar ratios by weight of human tissue. Preferably the human tissue molar ratio of composition of these components are at least 95 percent by weight and five percent by weight or less not strictly corresponding to the molar ratio of human tissue, and most preferably the human tissue molar ratio component composition corresponding to over 99% by weight and 1% or less not strictly corresponding to the molar ratio of human tissue.

The prior embodiments documented such as but not limited to the reversal of the need for skin graft in wound treatment of a Crohn's patient (exemplified by adding deficient vitamin A locally to anabolic counter collagenase stimulated by long-term corticosteroids along with wound healing anabolic zinc in the form of zinc oxide in the local and systemic anabolic therapy using locally and systemically subject to position synthetic stem cell-like medicament. Resulting in mechanisms also associated with the successful reduction in the need for long-term corticosteroid observer, in 85 percent of the 450 patients studied.

The subject composition also provided for a marked reduction in the necessity for major abdominal surgery (excisional bowel surgery and correction of fistulization is required in 70 percent of pediatric Crohn's disease patients in a period of conventional therapy five year care (data provided by the Ileitis Foundation of America) as exemplified by a 60 percent reduction in the need for correction of fistula by surgical care. In the 40 percent remaining that require major abdominal bowel surgery this therapy offers a further 55 percent reduction in surgical mortality.

Pediatric Crohn's disease is a disease of hereditary predisposition; however if this specific anti-inflammatory treatment is discontinued after one month of therapy (as might occur in the management of children considering stomach tube administration in the past), the absence of recurrence is noted to be as long as six months in those that discontinued treatment (70 percent fortunately do not recur in 7 to 12 months of further observation after discontinued treatment). This is suggestive of a genetic therapeutic component associated with this treatment.

The therapeutic application of the subject compositions also provide anti-inflammatory therapeutic responses without the usual associated complication of impairment of tissue protein synthesis and thereby further aggravation of negative nitrogen balance.

Documented studies here showed that further correction of these deficiencies added to any therapeutic plan added significantly to the prevention of this disease's significant predisposition for recurrences. Also included were enzymatic therapy and essential omega-3 EPA fatty acid fats with their contribution to this anti-inflammatory therapy as well as the addition of extracellular matrix (ECM), and reversal of impaired healing (associated with pediatric Crohn's disease and long-term steroids).

The addition of these deficiency corrections would further add to the management of this formerly intractable vicious progressive chronic granulomatous disease pediatric Crohn's disease in the growing child. Potentially contributing to the 15% of patients (vs. the 85%) that were not able to replace corticosteroids.

The components of the subject invention can, in some embodiment, be combined to form compositions. For Example, components #1 and #3 can be useful for anti-inflammatory or healing. Component #1 can be used to aid in protein formation and component #2 can be used to replace damaged cell membranes. Component #3 increases tensile strength of wound by 48% in more than 100 patients multi-center and double-blind, as well as in controlled animal studies and component #2, modified PC lysolecithin triggers onset of protein synthesis working synergistically with component #1.

Liquid crystal high HLB surfactants HLB>13 specifically 15-16 to 20 with a high packing parameter of less than ½ and contributing a high repulsive of charge zeta potential along with an increase in surface area and thereby synergize enzymatic activity of enzyme in association with a substrate, (thereby synergizing component #5) and as an anti-cancer agent also down modulating mitosis (in vitro documentation in prior embodiments) and especially in the use of Tween 80 containing 20 moles (or more) of ethylene oxide a maturation factor highly useful in the stimulation of apoptosis, a highly useful anti-cancer feature. The anti-cancer therapeutic features may be used alone or in conjunction with components 1, 2 and 3 as well as components one, two, three, four and five.

These subject compositions may be administered orally or parenterally or locally and in special applications as in anti-cancer may even be administered intra-arterially as therapy used in conjunction with routine medications to reduce side effects and synergize these companion medications and thereby lessen the dose required of routine medications.

In simulating all stem cell biochemical biophysical features simulated results as evidenced by averting need for an organ transplant while avoiding key stem cell side effects:
 (1) Bioethics independent of use of human embryonic tissue, but can build and rebuild thereby enhancing tissue healing, protein synthesis on existing tissue and in-vitro recombinant DNA tissue culture,
 (2) Avoiding the risk of transmission of such diseases as AIDS and Hepatitis and even cancer cells (incipient),
 (3) Avoiding the risk of rejection reaction and the need for HLA cross matching,
 (4) Adding a significant anti-tumor anti-cancer effect,
 (5) Sourcing has avoided the risk of allergic reaction by avoiding protein or substances that would cross match the patient's genetic code,
 (6) May be used freely with other medication to reduce their significant risk and dosage of medication.

In certain embodiments of the subject invention, a composition comprising: a) at least one glycosaminoglycan, proteoglycan aggregate complex of hyaluronic acid, extracellular matrix, protein and chondroitin, extracellular matrix compound in an amount effective in the damaged tissue as an anti-neo-inflammatory and anti-neo-angiogenetic agent; b) about one to three grams of at least one polar surface active lipid selected from the group consisting of phosphatidic acid, phophatidylethanolamine, lecithin, phosphatidylserine, phosphatidylinositol, 2-lysolecithin, plasmalogen, choline plasmalogen, phosphatidylglycerol, diphosphatidylglycerol, sphingomyelin, and any combination of 2, 3, 4, 5, 6, 7, 8, 9, 10 of said polar active surface lipids; c) a plurality of enantiomerically pure D-amino acids and glycine of about 9 to 25 grams; d) a component selected from the group consisting of polyoxyethylene Sorbitan Monooleate (TWEEN 80), Sorbitan monooleate, grape seed extract, grape extract, and combinations thereof; and e) vitamins, minerals or trace elements selected from the group consisting of Vitamin B12, Vitamin E, selenium, zinc, and combinations thereof is provided. Compositions of the subject invention can further comprise a compound generally accepted as safe (GRAS) selected from the group consisting of aspartame perfluorocarbon resins, perfluorocarbon cured elastomers. [alpha]-Amylase enzyme preparation from *Bacillus stearothermophilus*, benzoic acid, bromelain, catalase (bovine liver), lactic acid, linoleic acid, potassium acid tartrate, propionic acid, stearic acid, tartaric acid, diacetyl tartaric acid esters of mono- and diglycerides, ammonium bicarbonate, ammonium carbonate, ammonium chloride, ammonium hydroxide, ammonium citrate, dibasic, ammonium phosphate, monobasic; ammonium phosphate, dibasic; bacterially-derived carbohydrase enzyme preparation; bacterially-derived protease enzyme preparation; bentonite; benzoyl peroxide; n-Butane and iso-butane; Calcium glycerophosphate; Calcium lactate; Calcium pantothenate; Calcium propionate; Calcium stearate; Carbon dioxide; Beta-carotene; Cellulase enzyme preparation derived from *Trichoderma longibrachiatum*; Clove and its derivatives; Cocoa butter substitute; Copper gluconate; Copper sulfate; L-Cysteine; L-Cysteine monohydrochloride; Dextrin; Diacetyl; Enzyme-modified fats; Ethyl alcohol; Ficin; Glucono delta-lactone; Corn gluten; Wheat gluten; Glyceryl monooleate; Glyceryl behenate; Glyceryl palmitostearate; Helium; Inositol; Insoluble glucose isomerase enzyme preparations; Isopropyl citrate; Animal lipase; Magnesium carbonate; Magnesium chloride; Magnesium hydroxide; Magnesium oxide; Magnesium phosphate; Magnesium stearate; Magnesium sulfate; Malt; Malt syrup (malt extract); Manganese chloride; Manganese citrate; Manganese gluconate; Manganese sulfate; Microparticulated protein product; Mono- and diglycerides; Monosodium phosphate derivatives of mono- and diglycerides; Niacin; Niacinamide; Nickel; Nitrogen; Nitrous oxide; Peptones; Pancreatin; Papain; Pectins; Pepsin; Potassium bicarbonate; Potassium carbonate; Potassium chloride; Potassium hydroxide; Potassium lactate; Propane; Pyridoxine hydrochloride; Rennet (animal-derived) and chymosin preparation (fermentation-derived); Riboflavin; Riboflavin-5'-phosphate (sodium); Sodium benzoate; Sodium carbonate; Sodium hydroxide; Sodium hypophosphite; Sodium lactate; Sodium metasilicate; Sodium propionate; Sodium sesquicarbonate; Sodium tartrate; Sodium potassium tartrate; Starter distillate; Stearyl citrate; Thiamine hydrochloride; Thiamine mononitrate; [alpha]-Tocopherols; Triacetin; Tributyrin; Triethyl citrate; Trypsin; Urease enzyme preparation from Lactobacillus fermentum; Vitamin A; Vitamin B12; Candelilla wax; Carnauba wax; Bakers yeast extract; Zein; Sulfamic acid; Clay (kaolin); Ferric oxide; Iron oxides; Japan wax; Tall oil; Alfalfa; Allspice; Almond, bitter (free from prussic acid); Ambrette; Angelica root; Angelica seed or stem; Angostura; Anise; Asafetida; Balm; Balsam of Peru; Basil; Bay leaves; Bay; Bergamot (bergamot orange); Bois de rose; Cacao; Camomile (chamomile); Capsicum; Caraway; Cardamom seed (cardamon); Carob bean; Carrot; Cascarilla bark; Cassia bark, Chinese; Cassia bark, Padang or Batavia; Cassia bark, Saigon; Celery seed; Cherry, wild, bark; Chervil; Chicory; Cinnamon bark, Ceylon; Cinnamon bark, Chinese; Cinnamon bark, Saigon; Cinnamon leaf, Ceylon; Cinnamon leaf, Chinese; Cinnamon leaf, Saigon; Citronella; Citrus peels; Clary (clary sage); Clove bud; Clove leaf; Clove stem; Clover; Coca; Coca: Coffee; Cola nut; Coriander; Corn silk; Cumin (cummin); Curacao orange peel; Cusparia bark; Dandelion; Dandelion root; Dill; Dog grass (quackgrass, triticum); Elder flowers; Estragole; Estragole; Estragon (tarragon); Fennel, sweet; Fenugreek; Galanga (galangal); Garlic; Geranium; Geranium, East IndianGeranium, rose; Ginger; Glycyrrhiza; Glycyrrhizin, ammoniated; Grapefruit; Guava; Hickory bark; Horehound (hoarhound); Hops; Horsemint; Hyssop; Immortelle; Jasmine; Juniper (berries); Kola nut; Laurel berries; Laurel leaves; Lavender; Lavender, spike; Lavandin; Lemon; Lemon balm (see balm).; Lemon grass; Lemon peel; Licorice; Lime; Linden flowers; Locust bean-Lupulin; Mace; Malt (extract); Mandarin; Marjoram, sweet; Mate 1; Menthol; Menthyl acetate; Molasses (extract); Mustard; Naringin; Neroli, bigarade; Nutmeg; Onion; Orange, bitter, flowers; Orange, bitter, peel; Orange leaf; Orange, sweet; Orange, sweet, flowers; Orange, sweet, peel; Origanum; Palmarosa; Paprika; Parsley; Pepper, black; Pepper, white; PeppermintPeruvian balsam; Petitgrain; Petitgrain lemon; Petitgrain mandarin or tangerine; Pimenta; Pimenta leaf; Pipsissewa leaves; Pomegranate; Prickly ash bark; Rose absolute; Rosa; Rose; Rose buds; Rose flowers; Rose fruit (hips); Rose geranium; Rose leaves; Rosemary; Rue; Saffron; Sage; St. John's bread; Savory, summer; Savory, winter; Schinus molle; Sloe berries; Spearmint; Spike lavender; Tamarind; Tangerine; Tannic acid; Tarragon; Tea; Thyme; Triticum; Tuberose; Turmeric; Vanilla; Violet flowers; Violet leaves; Violet leaves absolute; Wild cherry bark; Ylang-ylang; and; Zedoary bark, or any combination of said compounds. Any combinations of the compounds GRAS can be used in formulating compositions of the subject invention. In some embodiments, the composition further comprises a flavorant that can be a fruit juice, such as tomato juice.

The following sections of Title 21 of the Code of Federal Regulations are hereby incorporated by reference in their entireties (with respect to materials generally recognized as safe (GRAS)): §§5, 25, 170, 172, 173, 177, 182, 184, 186, 570, and 582.

EXAMPLES

The following examples are used to illustrate preferred embodiments of the invention and are not meant to limit the scope of the invention in any way.

Example 1

Example of Multi-Center Study

Within three to six weeks of initiation of this treatment using the compositions of the invention, 85% of CD and PCD patients studied in double-blind, placebo-controlled multi-center including 35 radiographically tagged inflammatory neutrophile permeability studies as well as the open study were able to discontinue the immune suppression therapy.

Remarkably, the discontinuance was not associated with relapse for a period of at least six months. Seventy percent maintained the disease-free state for as long as one year. Growth arrest and puberty suppression were overcome within six weeks in more than 20 patients with a predictable efficacy of over 90% in. 150 patients (⅓ of 450 studied; PCD cases treated exceed 200 patients). Controlled in vitro tissue culture studies of biopsied Crohn's tissue evidenced 'significant 80% reduction in inflammatory mediator chemokines relative to controls after 24 hours.

The compositions also avert the need for surgery to address another Crohn's Disease complication (intestinal fistulae) in more than 60 percent of the cases, and in those cases that require surgery more than 50 percent reduction in surgical mortality with use of the subject composition.

Example 2

Example of CBA

Therapy with the compositions of the invention in one CBA patient using components #1 and #2 re-established organ function, -stimulated tissue healing and tissue protein synthesis concurrent with significant anti-inflammatory activity, clearance of all abnormal liver function. Liver ultrasound resulted in cancellation of scheduled liver transplant, averting liver transplant.

Example 3

Crohn's Disease, Case Report, Part (A)

A 71 year old female patient with more than 3 decades of Crohn's disease recently had a flare up of the Crohn's disease, unsatisfactory response from 4 mg of corticosteroid, once daily then increased to 4 times daily for acute flare ups. These flare ups prior to adding stem cell-like therapeutic three component composition, #1 and #2 in infant Neocate, SHS, L-amino acid glycine analog to mimicking the molar ratio of breast milk, 10 to 25 grams 2 to three times daily were effective in preventing flare ups and the need for an increase in corticosteroid 4 with its multiplicity of serious side effects to 4× daily 1-2 day, 3×d 1-2 day, 2×d 1-2 day, 1× daily maintenance dosage. The patient had been receiving 5-10 to 25 grams of L-amino acid and glycine, analogue molar ratio according to the genetic code to breast milk and lecithin (phospholipid-PC), responded to the addition of the third component extracellular matrix, collagen, proteo-glycan aggregate complex of cartilage and chondrotin sulfate (shark cartilage 740 mg. per capsule, 4 capsules twice daily). Thereby, analogue to and more completely mimicking human tissue adding stem cell like therapeutic three component composition for an acute flare-up of the acute symptoms of abdominal pain and diarrhea cleared within 24 hours and the improvement continued the past few weeks responding to the least amount of corticosteroids (alternating daily dosages of a half a tablet (2 mg) with a full tablet (4 mg), the least corticosteroids required to prevent flare-ups in the past several decades of management.

This reduction in dosage is mandatory because of the severe unsightly bruising and poor healing of lacerations and associated intolerance of sutures inducing even further bruising with a mimicking the healing of lacerations even more difficult (a common complication associated with long-term corticosteroids even if the dosage is only one tablet daily; having refused 6 mercaptopurine offered by her consulting gastroenterologist because of the possible complication of cancer). Her lacerations have been most successfully healed with non suture steristrips providing successful, and most amenable, addition of bringing the edges of the laceration in closest approximation because of the abnormal retraction of the wound (a difficulty observed in the corticosteroids treated patients in contrast to normal contraction of the wound). A therapeutic measure not noted in the prior art.

Another therapeutic component, comprising 2.1 grams of omega 3 seed oil (flax oil, sunflower oil, sesame seed oil), 1.7 grams of omega 6 oil, and 1 gram omega 9 oil (Flora brand), with the following well tolerated preferred recent substitute of omega 3 fish oil and seed oil (2 capsules 1-2 times daily), Thera Tears, serving size 2 softgels per serving, containing per 2 capsule Vitamin E (as D-alpha tocopherol concentrate) 100 IU (anti-rancidity antioxidant), Organic Flaxseed Oil 500 mg., EPA (Eicosapentaenoic Acid) (from Fish Oil) 225 mg, and DHA (Docosahexaenoic Acid) (from Fish Oil) 50 mg has also added to components #1 and #2. The anti-rancidity antioxidant vitamin E present in this capsule prevents the development of catabolic products that are counter to the components of this therapeutic innovation accounting for the tolerance of this fish oil product.

This patient is one of the unusual patients intolerant to the preferred of therapeutic component #2 polar surface active lipid anti-inflammatory component fish oil. Patients with ileitis have a deficiency of pancreatic lipase and enteric coated fish oil capsules may be more helpful in overcoming this intolerance. Oral mucosal delivery system of prior embodiments may also be useful as in prior embodiments and lipase supplied would be of salivary gland origin. This anti-inflammatory immune modulatory pharmacologic activity is furthered by the synergistic anti-oxidant vitamin A 5,000 units, 250 ml. of vitamin C, 400 ml. vitamin E (D-alpha tocopherol) and selenium 20 mg and Zinc 15 mg. This effect can be seen when used locally in this patient as a local application of zinc oxide in stimulating healing of skin trauma and when used to minimize the need for antibiotics, in the treatment of acute respiratory infections, and to provide similar protective effect prior to dental care in the form of zinc, glycine with optional Echinacea.

It should be noted here that significant progress has been made here and in these foregoing embodiments in masking a major problematic taste of the amino acid component which formerly, in the prior art, brought about the requirement of gastric tube administration and associated hospitalization.

Encapsulation of the medication would eliminate use of the gastric tube by by-passing the problematic taste of the amino acid component. However, for the pediatric or adult patient who can not take capsules, a vegetable flavored juice such as, but not limited to, tomato juice or V8 could be used as a flavored vehicle. One heaping teaspoon (approximately 5 grams) to 5 ounces of juice, was found by a taste panel to thoroughly mask the most objectionable taste of the first component, the amino acid product. This amino acid component includes, but is not limited to, Neocate for Infant use. This Crohn's patient was included in our taste panel in our attempt to improve the palatability of the objectionable amino acid component of subject composition.

Case Report: Example 3, Part (b) Crohn's Disease

Further response to addition of therapeutic components #4 and #5 (All 5 component therapeutic composition response).

Further progress report and addition of components #4 and #5 to this patient care added even further to significantly improve her clinical course. The addition of components #4 and #5 have provided for normalization of enzyme composition secretion of the tissue and the normalization of the microorganism flora with associated normalization of function of this gastrointestinal Crohn's diseased tissue has made possible for this patient for the first time to further reduce from one tablet of the corticosteroid that this three component therapy has permitted to use ½ tablet of corticosteroid (triamcinalone generic) for the first time in three decades without usual further steroid withdrawal symptoms of arthralgia common in steroid withdrawal as noted repeatedly in this patient in the past unsuccessful attempts of steroid reduction.

The side effects this patient has sustained from long-term corticosteroids has been worsening of osteoporosis documented by two successive bone scans two years apart, recurrent bruising and failure to heal including two threats of the need for skin graft which this subject composition stem cell-like treatment has prevented. Bruising and healing time of skin trauma as well as GI flare ups of diarrhea greatly improved.

Example 4

Countering Wound Healing Impairment with Steroids

The prior embodiments documented the reversal of the need for skin graft in wound treatment of a Crohn's patient (exemplified by adding deficient vitamin A locally to anabolic counter collagenase stimulated by long-term corticosteroids) along with wound healing when zinc, in the form of zinc oxide, was added to composition #5.

Example 5

Orthopedic and Anti-Arthritic Subject Composition Therapy—Case Report

A female patient age 48 has been treated for acute degenerative arthritis right hip confirmed by x-ray findings. Acute onset, May of 02 associated with progressive pain limping and requirement of support with a cane temporarily relieved by anti-inflammatory drug Vioxx with x-ray findings of severe inflammatory degenerative arthritis associated with absence of joint space of right hip joint and clinical regression right hip. Joint prosthetic replacement even though only age 48 was recommended by rheumatologist and orthopod. Patient refused surgical care and responded with use of extracellular matrix:

ECM: Glucosamine 750 mg. daily, Shark cartilage 450 mg., Cartilage 50 mg, gelatin, a denatured collagen, porcine origin, 1 to 2 tablespoons in fruit juice.

The addition of an anti-inflammatory immune modulator (omega 3 flax-seed oil, 1000 mg) provided a progressive response with reappearance of the hip joint space on x-ray (severe inflammatory changes had interfered with visualization of any joint space). Since the patient is now pain-free and no longer requires a cane supportive of walking, however still had a mild limp, the completion of the synthetic stem cell first and second component chiral L amino acid and non chiral glycine in the molar ratio of human tissue supportive of the stem cell, along with polar surface active lipid as phospholipid lecithin was suggested in the form of Neocate progressing from 5 grams daily to 15 grams daily to three times daily. It is expected that this additional therapy should significantly add to the therapeutic response progression.

Anti-inflammatory, immune modulatory bio-efficacy, bio-safety and pharmacologic activity is present with all four components of synthetic stem cell therapeutic subject composition.

Example 6

Inactivation of Cat Dander Allergen of Cat, to Lessen Respiratory Allergy Symptomatomatology after Cat Exposure (with Therapeutic Component #2)

High HLB liquid crystalline phase semi-conductor bio-computer used here and its biophysical hydrophilic micellar counterpart with its anti-allergenic subject composition therapeutic embodiments, in vitro basophilic de-granulation measure by histamine release comparing efficacy of treated cat dander in preventing histamine release with untreated cat dander when exposed to serum from cat allergic patients.

Example 7

The Use of High HLB Surfactant in Cancer May be Used Alone or as an Optional Component of Component #2

Comparative studies of inactivation of in-vitro cancer using tissue culture techniques with high HLB surfactant, Tween 80 are illustrated in Table 1.

Results of Treating T47D breast cancer tissue cells (Normalized):

TABLE 1

MTS (Breast cancer Mitochondrial activity Assay)

| | Culture Time | | % normalization |
|---|---|---|---|
| | 24 h | 48 h | of Breast cancer cells |
| Control | 1.0 | 1.0 | 0% |
| **Tween 80 (0.125%) | 0.48 | 0.24 | 76% |
| PC (0.125%) | 0.92 | 0.98 | |
| Tween 80 + PC (0.125% + 0.12596) | 0.61 | 0.42 | 58% |
| GS-1 (grape seed Extract, 0.5 mg 1-ml | 0.29 | 0.17 | 83% |
| Tween 80 + GS-1 | 0.27 | 0.17 | 83% |
| PC + GS-1 | 0.34 | 0.17 | 83% |

Breast cancer (Comparative histopathologic studies before and after treatment with high HLB Tween 80 surfactant
**Histopathologic studies correlate with a more than 50% reduction of cancer cells seen after 48 hours of treatment with 0.125% Tween 80.

Summary of Cell Inhibition Assays

Development of metastatic cancer involves several steps, usually separated in to initiating and promotional steps. Initiation involves somatic mutation leading to altered expression of genes controlling DNA synthesis and cell replication. Promotion involves stimulation of the mutated cell to continued division. Subsequent mutations in these altered cells lead to more aggressive replication and invasion of neighboring tissues. In many tumors, the tumor cells are cycling while their neighbors are in the GO phase of the cell cycle. Substances which interfere with mutagenesis or with cell division could prove to be anti-carcinogenic.

Several extracts of these for their abilities to inhibit the metabolism of cells isolated from breast and cervical cancer tissue have been examined in regard to the anti-cancer effects of extracts which have proven capable of significantly inhibiting the metabolism of these cancer tumor cells. In addition to and equal to the effects of high HLB surfactants for comparative testing. These comparative studies were performed and results are reported in the above table. Metabolism was comparatively measured with controls and other extracts as to the reduction of mitochondrial activity, (MTS). This compound is a substrate for the mitochondrial enzymes—and is reduced to a blue formazan product.

Activity of the extracts was tested with the MCF-7 and T47-D breast cancer cell lines and against the CaSki and SiHa cervical cell lines. During the later experiments, the CRL 7367 and CRL 7368 cell lines became available and were included in subsequent trials. CRL 7368 is a line established from transformed fibroblasts isolated from a breast cancer. CRL 7367 was established from apparently healthy skin fibroblasts taken from the same donor.

Methods

In the first experiments—The extracted therapeutic test agents were derived from specified tissue. Water extracts of the crushed tissue, were also prepared. For the later experiments, specific varieties of extracts were prepared and examined: Cells were obtained from American Type Culture Collection (ATCC, Washington, D.C.) and were cultured as recommended by ATCC. Experiments were performed in 96 well microtiter plates. Each well contained $1.0 \times 10^4$ cells suspended in a total volume of 200 ml. Test wells contained the designated amount of extract in cell culture medium. Control wells contained the same amount of extract solvent in medium. Plates were incubated in an atmosphere of 5% $CO_2$ for 24 or 48 hours with extract or solvent. At this time,—pl— (MTS) were added to each well and incubation was continued for an additional 4 hours after which time the optical density (OD) at nm of each well was recorded. In each experiment, each sample was assayed in triplicate and the mean optical density (OD) for the three wells containing the same culture was calculated.

Results

Data are presented as suppression ratios. The suppression ratio defined here as the mean optical density (OD) for the wells containing extract divided by the mean optical density (OD) for the control wells. A value of this ratio of 1.0 indicates that the extract had no effect on metabolism of the cells being tested. A value of less than 1.0 indicates inhibition of cell metabolism by the extract or the high HLB surfactant Tween 80.

The purpose of the work was to determine which therapeutic agent extracts (further separated by chromatography) explored through this methodology for anti-cancer activity. The data presented here represents semi-quantitative anti-cancer screening tests. Extracts with ratios in the range 0.51-0.74 were considered moderately active and therefore appropriate for considered use along with preventive anti-cancer treatment and active anti-cancer treatment. In co-use with anti-cancer treatment and radiation treatment, may lessen the dose and the side effects of these current therapeutic agents. Extracts with metabolism suppression ratios less than or equal to 0.5 represented a suppression of metabolism of at least 50% or greater than that of the controls and were considered definitely active potential anti-cancer agents, as was the case of High HLB Tween 80 with ethylene maturation apoptosis promoting factor with a 76% suppression of mitochondrial metabolism of cancer cells.

In the first experiments, tissue extract prepared in the laboratory and water extract from tissue commercially obtained were, comparatively examined. These results were presented in Table 1. The data indicated that comparatively both therapeutic agents derived from tissue extracts freshly prepared in this laboratory and water extract inhibit can cell metabolism at the higher concentrations tested. There is a clear dose effect indicating that therapeutic agents derived from tissue extracts prepared in our laboratory at concentrations lower than 0.004 and commercially available water extract concentrations lower than 0.02 do not inhibit metabolism. Data for alcohol extracts were also presented. The extracts had minimal effects on metabolism after three days of treatment, but after five days of treatment the ethanol extract had inhibited metabolism of both breast cancer cell lines by over 60%. Some extracts suppressed the MCF-7 cell One, but had minimal effect on the T47-T cell line or on the cervical cancer cell lines even when the extract anti-cancer treatment agent composed 4% of the total culture volume. Of all the extracts examined the tissue extract anti-cancer treatment agent obtained with 70% acetone/30% water was the most active.

Acetone is an agent used in separating phospholipid surfactants, e.g. phosphatidylcholine (PC), phosphatidyl serine (PS), phosphatidyl inositol (PI), and phosphatidyl ethanolamine (PE) acetone insoluble representing 58% of surfactants present in soy lecithin. 70% acetone and 30% water used here as a tissue extracting agent is most probably a hydrophilic surfactant.

Example 8

Case Report—Therapeutic Composition to Counter Withdrawal Symptoms and Side Effects of Medications and Drugs and Drug Addiction and Dependency The Therapeutic Results and Rationale for inclusion of Components #4 and #5: This detailed therapeutic replication of normal human tissue (and therefore complete reversal of disease tissue) and by including the products of therapeutic components #4 and #5, (added to components #1, #2, and #3 past month and added past two months to care of prior patient), normalization of enzyme composition secretion of the tissue and the normalization of the micro-organism flora with associated normalization of function of this gastrointestinal Crohn's diseased tissue has made possible for this patient for the first time (and not reported or taught in that art) to further reduce from one tablet of the corticosteroid that this three component therapy has permitted to use ½ tablet instead of corticosteroid (triamcinalone, common generic) for the first time in three decades without usual further steroid withdrawal symptoms of arthralgia common in steroid withdrawal as noted repeatedly in this patient in the past unsuccessful attempts of steroid reduction.

The side effects this patient has sustained from long-term corticosteroids has been worsening of osteoporosis documented by two successive bone scans to years apart, recurrent bruising and failure to heal including two threats of the need for skin graft which this subject composition stem cell-like treatment has prevented. Bruising and healing time of skin trauma as well as GI flare ups of diarrhea greatly improved.

These therapeutic compositions may also be specifically applied to addiction by mimicking normal tissue metabolism and normal tissue including the L-amino acid glycine molar ratio of endorphin to metabolically stimulate and in fact coerce, by the law of mass action, the proteins assemblage system of the body to produce this hormone. Since one mole of tyrosine, two moles of glycine and one mole of phenylalanine seem to be essential for the narcotic effects of beta endorphin and the met and leu-enkephalins, this anti-addiction effect then would be compared to the complete L-amino acid glycine molar ratio of beta endorphin. This molar ratio of beta endorphin also includes one mole of methionine, two moles of threonine, two moles of serine, four moles of lysine, two additional moles of phenylalanine, one mole of glutamine, one mold of proline, one mole of valine, one mole of leucine, two moles of asparagine, two moles of alanine, two moles of isoleucine, one mole of tyrosine, one mole of glycine, and one mole of glutamic acid.

The same principles and therapeutic components have been applied in normalizing, as noted in prior embodiments, dependency or withdrawal symptoms such as, but not limited to, the use of drugs in controlled substances, alcohol and/or drug and tobacco addiction in the medical patient or veterinary practice or experimental conditions such as the animal or tissue culture.

Therefore, these therapeutic compositions form a clinical bridge beyond other advanced technologies that have not to date found a clinical application with exemplary bio-safety.

I claim:
1. An anabolic composition comprising:
    a) proteoglycans, cartilage, chondroitin sulfate, hyaluronic acid, collagen, glycosaminoglycan, extracellular matrix proteoglycan aggregate complex, an extracellular matrix compound or combinations thereof;
    b) at least one polar surface active lipid selected from the group consisting of phosphatidic acid, phosphatidylethanolamine, lecithin, phosphatidylcholine, phosphatidylserine, phosphatidylinositol, 2-lysolecithin, lysolecithin, plasmalogen, choline plasmalogen, phosphatidylglycerol, diphosphatidylglycerol, sphingomyelin, and any combination of 2, 3, 4, 5, 6, 7, 8, 9, 10, or 11 of said polar active surface lipids;
    c) a plurality of enantiomerically pure L-amino acids and glycine, wherein the plurality of L-amino acids and glycine are in molar ratios corresponding to endorphins;
    d) taurine or L-carnitine or both taurine and L-carnitine;
    e) a surfactant having a hydrophilic/lipophilic balance (HLB) greater than 8; and
    f) vitamins, minerals or trace elements selected from the group consisting of vitamin A, vitamin B12, vitamin D, vitamin E, niacin (vitamin B3), pyridoxine hydrochloride (vitamin B6), magnesium, folic Acid, vitamin E, ascorbic acid, selenium, zinc, and combinations thereof.

2. The composition according to claim 1, further comprising a compound generally recognized as safe (GRAS), said compound being garlic.

3. The composition according to claim 1, further comprising a flavorant.

4. The composition according to claim 3, wherein said flavorant is a fruit juice.

5. The composition according to claim 4, wherein said flavorant is chocolate.

6. The composition according to claim 4, wherein said fruit juice is tomato juice.

7. The composition according to claim 1, wherein said plurality of L-amino acids and glycine are selected from L-Leucine, L-Proline, L-Valine, L-Isoleucine, Glycine, L-Threonine, L-Tyrosine, L-Phenylalanine, L-Serine, L-Histidine, L-Alanine, L-Lysine, L-Methionine, L-Glutamine, L-Asparagine, L-Glutamic Acid or combinations thereof.

8. The composition according to claim 1, wherein said component (b) comprises soy lecithin.

9. The composition according to claim 1, wherein said composition comprises taurine.

10. The composition according to claim 1, wherein said composition comprises L-carnitine.

11. The composition according to claim 1, wherein said composition comprises both taurine and L-carnitine.

12. The composition according to claim 1, wherein said composition further comprises omega-3 fatty acids.

13. The composition according to claim 1, wherein said composition further comprises one or more compound generally recognized as safe (GRAS).

14. The composition according to claim 1, wherein said composition comprises phosphatidylcholine.

15. The composition according to claim 1, wherein component (b) comprises lecithin.

16. The composition according to claim 1, wherein component (b) comprises lysolecithin.

17. The composition according to claim 1, said composition further comprising a probiotic composition comprising probiotic microorganisms.

18. The composition according to claim 17, wherein said probiotic composition comprises *Lactobacillus acidophilus* DDS-1, *Bifidobacterium bifidum, Lactobacillus bulgaricus* or *Lactobacillus salivarius*.

19. The composition according to claim 1, wherein said surfactant is selected from the group consisting of polyoxyethylene sorbitan monooleate, sodium lauryl sulfate, grape seed extract, grape extract and combinations thereof.

20. The composition according to claim 1, wherein said L-amino acids are selected from L-histidine, L-lysine, L-glutamine, L-asparagine, L-glutamic acid, or combinations thereof.

21. The composition according to claim 1, wherein said surfactant has an HLB greater than 13.

22. The composition according to claim 21, wherein said surfactant has a surfactant packing parameter of less than ½.

23. The composition according to claim 21, wherein said surfactant has an HLB of 15-20.

24. The composition according to claim 23, wherein said surfactant has a surfactant packing parameter of less than ½.

25. The composition according to claim 1, further comprising a compound generally recognized as safe (GRAS), said compound being tea extract.

26. The composition according to claim 1, wherein said surfactant has a surfactant packing parameter of less than ½.

27. The composition according to claim 1, wherein said composition further comprises L-Arginine, L-Aspartic Acid, L-Tryptophan, L-Cysteine and/or L-Cystine.

28. A method of treating an inflammatory bowel disease comprising administering an effective amount of the composition according to claim 1 to an individual having an inflammatory bowel disease, thereby treating the inflammatory bowel disease.

29. The method according to claim 28, wherein said inflammatory bowel disease is Crohn's disease.

* * * * *